United States Patent [19]
Silvestrini

[11] Patent Number: 5,824,086
[45] Date of Patent: Oct. 20, 1998

[54] SEGMENTED PRE-FORMED INTRASTROMAL CORNEAL INSERT

[75] Inventor: Thomas A. Silvestrini, Alamo, Calif.

[73] Assignee: KeraVision, Inc., Fremont, Calif.

[21] Appl. No.: 718,291

[22] Filed: Sep. 20, 1996

Related U.S. Application Data

[63] Continuation of Ser. No. 559,892, Nov. 2, 1995, abandoned, which is a continuation of Ser. No. 101,438, Aug. 2, 1993, abandoned.

[51] Int. Cl.$^6$ .................................................. A61F 2/14
[52] U.S. Cl. ............................................... 623/5; 606/107
[58] Field of Search ............................ 623/4, 5; 606/107

[56] References Cited

U.S. PATENT DOCUMENTS

| | | | |
|---|---|---|---|
| 3,915,172 | 10/1975 | Wichterle et al. . | |
| 4,014,335 | 3/1977 | Arnold | 424/427 |
| 4,290,426 | 9/1981 | Luschen et al. | 128/260 |
| 4,452,235 | 6/1984 | Reynolds | 623/5 |
| 4,671,276 | 6/1987 | Reynolds | 623/5 |
| 4,688,570 | 8/1987 | Kramer et al. | 128/305 |
| 4,693,939 | 9/1987 | Ofstead | 428/421 |
| 4,766,895 | 8/1988 | Reynolds | 623/5 |
| 4,781,187 | 11/1988 | Herrick | 623/5 |
| 4,815,463 | 3/1989 | Hanna | 128/751 |
| 4,851,003 | 7/1989 | Lindstrom | 623/5 |
| 4,936,825 | 6/1990 | Ungerleider | 604/8 |
| 4,941,093 | 7/1990 | Marshall et al. | 364/413.01 |
| 4,961,744 | 10/1990 | Kilmer et al. | 606/166 |
| 5,067,961 | 11/1991 | Kelman et al. | 623/5 |
| 5,090,955 | 2/1992 | Simon | 604/51 |
| 5,098,443 | 3/1992 | Parel et al. | 623/4 |
| 5,147,647 | 9/1992 | Darougar | 424/427 |
| 5,171,265 | 12/1992 | Kelley | 623/4 |
| 5,178,635 | 1/1993 | Gwon et al. | 623/4 |
| 5,372,580 | 12/1994 | Simon et al. . | |
| 5,403,335 | 4/1995 | Loomas et al. | 606/161 |

FOREIGN PATENT DOCUMENTS

| | | |
|---|---|---|
| 1 771 730 | 10/1992 | Russian Federation . |
| 388746 | 7/1973 | U.S.S.R. . |
| 1209211 | 7/1986 | U.S.S.R. . |
| 2095119 | 9/1982 | United Kingdom . |
| WO 93/13724 | 7/1993 | WIPO . |

OTHER PUBLICATIONS

English translation of Brazilian Patent Publication No. BR 8705060 (Mar. 21, 1989).

Temirov et al., "Refraction ring–like tunnel keroplasty in the correction of high myopia" *Vestnik Oftalmologii* (1991) 3:21–31.

Nataloni, "Gel injection adjustable keroplasty shows promise" *Occular Surg. News* (Mar. 1997) 1 page total.

Avetisov et al., "The regularities and causes of changing corneal curvature after the surgery of recti muscles of the eye" UDC 617.761–009.11–089–06:617.713.5–02–07, pp. 24–26. A partial English abstract is located on p. 26 and a complete Russian–to–English translation is also attached.

Gonchar et al., "Interlayer refraction tunnel keratoplasty in the correction of myopia and astigmatism" UDC 617.753.2–617.753.3 089:617.713–089.844 (1984) pp. 25–30. A partial English abstract is located on p. 30 and a complete Russian–to–English translation is also attached.

Choyce et al., "Additional thoughts on polysulfone corneal inlays" *J. Cataract. Refract. Surg.* (1977) 23:8–9.

Crawford et al., "Preliminary evaluation of a hydrogel core–and skirt keratoprosthesis in the rabbit cornea" *J. Refract. Surg.* (1996) 12:525–529.

(List continued on next page.)

*Primary Examiner*—Randy C. Shay
*Attorney, Agent, or Firm*—Morrison & Foerster, LLP

[57] ABSTRACT

This invention is a pre-formed intrastromal corneal insert. It is made of a physiologically compatible polymer and may be used to adjust corneal curvature and thereby correct vision abnormalities. The insert or segment may also be used to deliver therapeutic or diagnostic agents to the interior of the cornea or of the eye. The insert subtends only a portion of a ring, or "arc", encircling the anterior cornea outside of the cornea's field of view. The invention also includes a procedure for inserting the device into the cornea.

54 Claims, 6 Drawing Sheets

OTHER PUBLICATIONS

Internet abstract of Linnola et al., "Titanium and bioactive glass–ceramic coated titanium as materials for keratoprosthesis" *Exper. Eye Res.* (1996) 63(4):471–478 from http://gateway.ovid.com/server1/(1 page total).

Parks et al., "Hydrogel keratophakia: Long–term morphology in the monkey model" *CLAO J.* (1991) 17(3):216–222.

Werblin et al., "Initial human experience with permalens® myopic hydrogel intracorneal lens implants" *Refract. & Corneal Surg.* (1992) 8:23–26.

SEGMENTED PRE-FORMED INTRASTROMAL CORNEAL INSERT

CROSS-REFERENCE TO RELATED APPLICATIONS

This application is a continuation of application Ser. No. 08/559,892, filed Nov. 20, 1995 (abandoned); which is a continuation of application Ser. No. 08/101,438, filed Aug. 2, 1993 (abandoned).

FIELD OF THE INVENTION

This invention is a pre-formed intrastromal corneal insert. It is made of a physiologically compatible polymer and may be used to adjust corneal curvature and thereby correct vision abnormalities. The insert or segment may also be used to deliver therapeutic or diagnostic agents to the interior of the cornea or of the eye. The insert subtends only a portion of a ring, or "arc", encircling the anterior cornea outside of the cornea's field of view but within the frontal circumference of the cornea, but may be used in multiples to form complete arcs or to form constructs of varying thicknesses. The invention also includes both a minimally invasive procedure for inserting one or more of the devices into the cornea as well as the thus-corrected eye.

BACKGROUND OF THE INVENTION

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. In contrast, when the front-to-back distance of eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea refracts light in a different meridian at different distances. Some degree of astigmatism is normal, but where it is pronounced, the astigmatism must be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

Another method for correcting those disorders is through the implantation of polymeric rings (intrastromal corneal rings) in the eye's corneal stroma to change the curvature of the cornea. Previous work involving the implantation of polymethylmethacrylate (PMMA) rings, allograft corneal tissue, and hydrogels is well documented. One of the ring devices involves a split ring design which is inserted into a channel previously dissected in the stromal layer of the cornea. A minimally invasive incision is used both for producing the channel and for inserting the implant. See, for instance, the use of PMMA intrastromal rings in U.S. Pat. Nos. 4,452,235 to Reynolds; 4,671,276 to Reynolds; 4,766,895 to Reynolds; and 4,961,744 to Kilmer et al. These documents suggest only the use of intrastromal corneal rings which completely encircle the cornea.

The use of soft polymers as intrastromal inserts is not widely known. For instance, U.S. Pat. No. 5,090,955 to Simon, suggests an intrastromal corneal ring which is made by introducing a settable polymer or gel into a previously made intrastromal channel. This procedure does not allow the surgeon to specify the precise size of the resulting ring nor is it a process which allows precise control of the pathway of the flowing polymer within the eye since the gel must simply conform to the shape of the intrastromal channel. However, it does show the concept of using arcuate channels containing a gel-based insert centered about the corneal to correct.

Temirov et al, "Refractive circular tunnel keroplasty in the correction of high myopia", Vestnik Oftalmologii 1991: 3-21-31, suggests the use of collagen thread as intrastromal corneal ring material.

These publications do not suggest the introduction of pre-formed polymeric arcuate inserts into the cornea for the correction of various visual aberrations. Certainly the publications do not imply that the devices may be used to introduce therapeutic or diagnostic materials into the corneal intrastromal space.

SUMMARY OF THE INVENTION

This invention is a pre-formed polymeric insert suitable for insertion between the lamella of the corneal stroma. The insert is an arc-shaped segment of a ring and may be used in isolation, in isolated multiples, in cooperative multiples, as segments in a larger assemblage encircling at least a portion of the cornea, or as assemblages to form constructs of varying thickness. The insert may be of one or more synthetic or natural polymers, hydrophilic or hydrophobic, or may be a hybrid device comprising layered materials or it may be hollow.

The insert may be adapted to be fillable with a biologic agent, drug or other liquid, emulsified, or time-release eye treatment or diagnostic material.

When the insert is a hybrid, both the inner and outer portions may comprise variously one or more high or low modulus, physiologically compatible polymers or a composite of a low modulus polymer and a high modulus polymer. The inner portion may comprise a gel or a polymeric material which is polymerized in situ after introduction into a hollow center layer.

These inventive segmented inserts may be introduced into the corneal stroma using techniques involving the steps of providing an intrastromal channel which traverses at least a portion of the circumcorneal rotation. Specific indications, such as astigmatism, may be rectified by insertion of one or more of the inserts into a partial intrastromal channel to flatten the steeper portions of the anterior corneal surface without insertion of a complete intrastomal corneal ring (or intracorneal ring).

If hydratable polymers are used, they may be hydrated before or after introduction into the intrastromal passageway created by the surgical device used to introduce these devices into the eye. If the outer layer is hydrated before insertion into the eye, the final size of the insert is set before that insertion. If the hydratable polymers are allowed to hydrate within the corneal space, the device (if appropriate polymers are chosen) will swell within the eye to its final size. If prehydrated, the outer layer often provides a measure of lubricity to the device, allowing it to be inserted with greater ease. Other of the noted low modulus polymers may also provide such lubricity.

BRIEF DESCRIPTION OF THE DRAWINGS

Each of FIGS. 4A, 4B, and 4C; 5A, 5B and 5C; 6A, 6B, and 6C; and 7A, 7B, and 7C, shows respectively a front view ("A"), a cross section ("B"), a top view ("C") of various narrow point intracorneal inserts made according to the invention.

DESCRIPTION OF THE INVENTION

Prior to explaining the details of the inventive devices, a short explanation of the physiology of the eye is needed to appreciate the functional relationship of these intracorneal inserts or segments to the eye.

Figure 1:
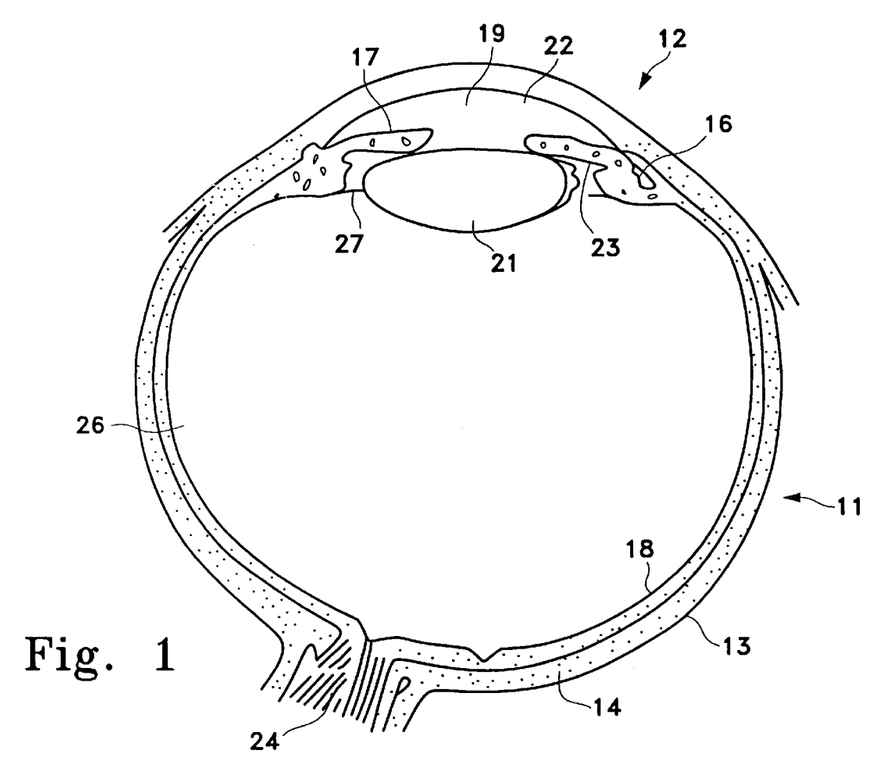
FIG. 1 is a schematic illustration of a horizontal section of the eye.

FIG. 1 shows a horizontal cross-section of the eye with the globe (11) of the eye resembling a sphere with an anterior bulged spherical portion representing the cornea (12).

The globe (11) of the eye consists of three concentric coverings enclosing the various transparent media through which the light must pass before reaching the light-sensitive retina (18). The outermost covering is a fibrous protective portion the posterior five-sixths of which is white and opaque and called the sclera (13), and sometimes referred to as the white of the eye where visible to the front. The anterior one-sixth of this outer layer is the transparent cornea (12).

A middle covering is mainly vascular and nutritive in function and is made up of the choroid, ciliary body (16), and iris (17). The choroid generally functions to maintain the retina (18). The ciliary body (16) is involved in suspending the lens (21) and accommodation of the lens. The iris (17) is the most anterior portion of the middle covering of the eye and is arranged in a frontal plane. It is a thin circular disc similar in function to the diaphragm of a camera, and is perforate near its center by a circular aperture called the pupil (19). The size of the pupil varies to regulate the amount of light which reaches the retina (18). It contracts also to accommodation, which serves to sharpen the focus by diminishing spherical aberration. The iris divides the space between the cornea (12) and the lens (21) into an anterior chamber (22) and posterior chamber (23). The innermost portion of covering is the retina (18), consisting of nerve elements which form the true receptive portion for visual impressions.

The retina (18) is a part of the brain arising as an outgrowth from the fore-brain, with the optic nerve (24) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (26) is a transparent gelatinous mass which fills the posterior four-fifths of the globe (11). At its sides it supports the ciliary body (16) and the retina (18). A frontal saucer-shaped depression (27) houses the lens.

The lens (21) of the eye is a transparent bi-convex body of crystalline appearance placed between the iris (17) and vitreous body (26). Its axial diameter varies markedly with accommodation. A ciliary zonule (273), consisting of transparent fibers passing between the ciliary body (16) and lens (21) serves to hold the lens (21) in position and enables the ciliary muscle to act on it.

Referring again to the cornea (12), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
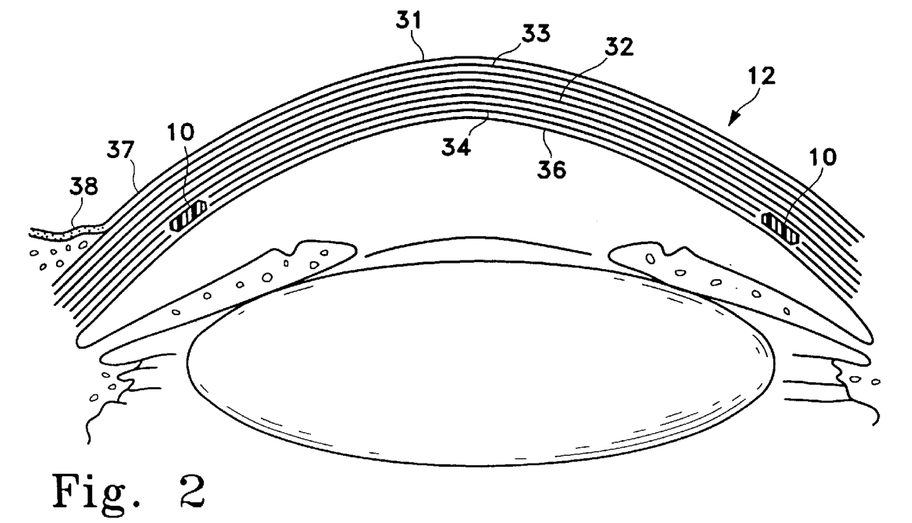
FIG. 2 is a schematic illustration of the anterior portion of the eye showing the various layers of the cornea.

FIG. 2 is a more detailed drawing of the anterior portion of the globe showing the various layers of the cornea (12) making up the epithelium (31). Epithelial cells on the surface thereof function to maintain transparency of the cornea (12). These epithelial cells are rich in glycogen, enzymes, and acetylcholine and their activity regulates the corneal corpuscles and controls the transport of water and electrolytes through the lamellae of the stroma (32) of the cornea (12).

An anterior limiting lamella (33), referred to as Bowman's membrane or layer, is positioned between the epithelium (31) and the stroma (32) of the cornea. The stroma (32) are made up of lamellae having bands of fibrils parallel to each other and crossing the whole of the cornea. While most of the fibrous bands are parallel to the surface, some are oblique, especially anteriorly. A posterior limiting lamella (34) is referred to as Descemet's membrane. It is a strong membrane sharply defined from the stroma (32) and resistant to pathological processes of the cornea.

A typically placed Intrastromal Corneal Ring (ICR) (10) is shown in FIG. 2.

The endothelium (36) is the most posterior layer of the cornea and consists of a single layer of cells. The limbus (37) is the transition zone between the conjunctiva (38) and sclera on the one hand and the cornea (12) on the other.

Figure 3A:
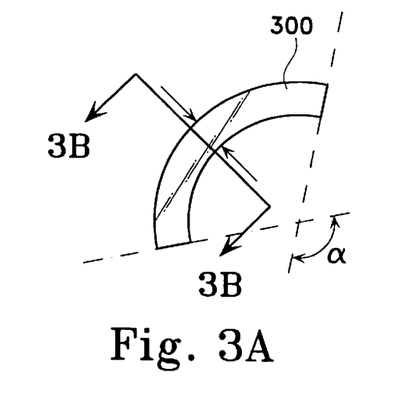
FIGS. 3A and 3B show respectively a front view and a cross section of a typical intracorneal insert made according to the invention which shows certain defined terms used in the description.
Figure 3B:
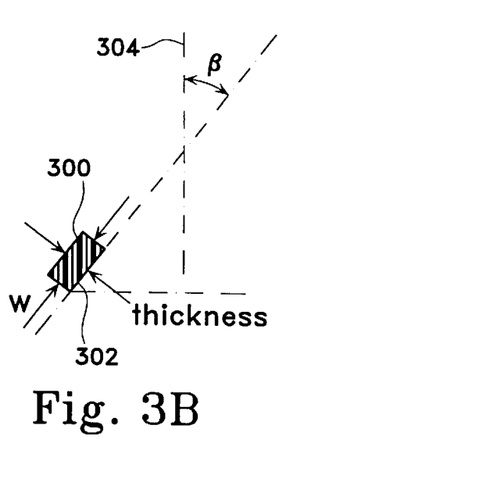

FIG. 3A shows a front view of a typical insert made according to the invention and FIG. 3B shows a cross section of that insert. The inventive insert is placed in an eye using a procedure similar to those shown in our copending applications having Ser. Nos. 07/867,745 entitled "Corneal Vacuum Centering Guide and Dissector" (attorney docket no. 25169-20006.00), now abandoned under 37 C.F.R. §1.62 in favor of continuation-in-part application Ser. No. 08/214, 654 filed on Mar. 15, 1994, now U.S. Pat. No. 5,403,335, and 07/927,165 entitled "Hybrid Intrastromal Corneal Ring"

(attorney docket 25169-20007.00), the entirety of which are incorporated by reference. These segments are suitable for insertion into the appropriately prepared interlamellar, intrastromal, intracorneal channel. Generally the intrastromal segment is installed in the following manner: A small radial incision is made at the corneal radius in which the intrastromal segment is ultimately to be installed about the cornea. A dissector in the form of a split ring having a point suitable for producing the interlamellar channel in the corneal stroma is introduced into the stromal space through the small incision. It is then rotated in such a fashion that a generally semicircular or arc-shaped channel is formed partially circling the cornea at the chosen radius. The dissector is then rotated in the opposite direction to withdraw it from the tunnel or channel thus formed. An intrastromal segment is then introduced into the channel.

As is shown in FIG. 3A, the arcuate segment (300) is a portion of the circle and subtends some specific amount of a circumference of the cornea (at some chosen radius) equal to a value of "α", which value is less than 360°, preferably less than 320°, most preferably less than 270°. I refer to this angle as the "arc angle". The value of "a" is dependent upon the indication to be resolved and the physical arrangement of the segment (or segments) as they are installed in the eye. For instance, often the value of "α" is 60° to 90° for the correction of modest astygmatic aberrations. In any event, for definitional purposes, the opposite ends of a single "segment" do not meet when the segment is inserted into an intrastromal channel.

Similarly, if the segments are joined or used in conjunction with each other (such as are described in discussing FIGS. 10, 11, and 12 below) the value of "α" may be any of a wide range of values up to and including 360° or more.

Similarly, FIG. 3B shows an orientation angle "β" of the segment as it is placed in the eye. Generally, the angle "β" is the angle between the tangent of the backside (302) of the segment (300) and the mean midline (304) of the eye. If the segment were (300) to be a continuous ring encircling the cornea, it would be known as a cone angle. For convenience, the chosen conventions for thickness and width are shown on FIG. 3B.

We have found that for the majority of uses to which these inserts are intended, the value of "β" may be between 0° and 90°, preferably between 20° and 45°. Generally, the value of "β" will be about 11° to 38°.

Further, the typical width is often between 0.005 inches and 0.250 inches. The typical thickness is often between 0.005 inches and 0.080 inches. Both of these parameters (along with certain other variables such as the cross-sectional shape of the device and its constituent polymers) determine, in large part, the level of correction achievable by use of a selected insert.

The materials used in these inserts may be relatively stiff (high modulus of elasticity) physiologically acceptable polymers such as polymethylmethacrylate (PMMA), TEFLON, polycarbonate, polysulfones, epoxies, or polyolefins such as polyethylene, polypropylene, polybutylene, and their mixtures and interpolymers. By "high modulus of elasticity", I mean moduli greater than about 3.5 kpsi. Many of these polymers are known in the art to be appropriately used in hard contact lenses. Obviously, any polymer which is physiologically suitable for introduction into the body is useful in the inserts of this invention. Many of the listed polymers are known to be suitable as hard contact lenses. For instance, PMMA has a long history in ophthalmological usage and consequently is quite desirable for use in these inserts.

Additionally, the polymeric material making up the segment may be low modulus polymers, e.g., those having a modulus of elasticity below about 3.5 kpsi, more preferably between 1 psi and 1 kpsi, and most preferably between 1 psi and 500 psi, which are physiologically compatible with the eye. Most polymeric materials used in soft contact lenses are suitable the segments of this invention. The class includes physiologically compatible elastomers and such crosslinked polymeric gels as polyhydroxyethylmethylacrylate (Poly-HEMA) or polyvinylpyrrolidone (PVP), polyethylene oxide, or polyacrylates, polyacrylic acid and its derivatives, their copolymers and interpolymers, and the like as well as biologic polymers such as crosslinked dextran, crosslinked heparin, or hyaluronic acid.

In many instances, the intrastromal segments may be hybrid, that is to say, the segments are made up of a number of polymeric layers typically with a soft or hydratable polymer on their outer surface. These hybrid segments will be described with greater particularity below. Partially hydrated or fully hydrated hydrophilic polymers are typically slippery and consequently may contribute to the ease with which the insert may be introduced into the interlamellar tunnel. It is usually desirable to (at least partially) hydrate the hybrid intrastromal segment in that, otherwise, the intrastromal segment during its traverse through the tunnel may desiccate the path and begin to stick to the interior wall of the tunnel. Suitable hydrophilic polymers include polydroxyethylmethacylate (pHEMA), N-substituted acrylamides, polyvinylpyrrolidone (PVP), polyacrylamide, polyglycerylmethacrylate, polyethyleneoxide, polyvinyl alcohol, polyacrylic acid, polymethacrylic acid, poly (N, N-dimethyl amino propyl-$N^1$-acrylamide) and their copolymers and their combinations with hydrophilic and hydrophobic comonomers, crosslinks, and other modifiers. Thermoplastic hydrogels include hydropolyacrylonitrile, polyvinyl alcohol derivatives, hydrophilic polyurethanes, styrene-PVP block copolymers and the like.

The intrastromal segment may be lubricated with suitable ocular lubricants such as hyaluronic acid, methylethyl cellulose, dextran solutions, glycerine solutions, polysaccharides, or oligosaccharides upon its introduction to help with the insertion particularly if one wishes to insert intrastromal segments of hydrophilic polymers without prior hydration. If a hybrid segment having a hydrophilic polymeric covering or a segment comprising a hydrophilic polymer is inserted into the eye without prior hydration, subsequent to the insertion, the intrastromal segment will swell to its final size or thickness within the eye. This swelling often permits the inclusion of larger intrastromal segments than would normally be accommodated within normal sized intrastromal channels.

Low modulus polymers used in this invention are often absorbent, particularly if they are hydratable, and may be infused with a drug or biologic agent which may be slowly released from the device after implantation of the intrastromal segment. For instance, the low modulus polymer may be loaded with a drug such as dexamethasone to reduce acute inflammatory response to implanting the device. This drug helps to prevent undesirable scarring or vascular ingrowth toward the intrastromal segment. Similarly, heparin, corticosteroids, antimitotics, antifibrotics, antiinflammatories, anti-scar-forming, anti-adhesion, and antiangiogenesis factors (such as nicotine adenine dinucleotide ($NAD^+$)) may be included to reduce or prevent angiogenesis and inflammation.

Clearly, there are a variety of other drugs suitable for inclusion in the intrastromal segment. The choice will depend upon the use to which the drugs are put.

Each of FIGS. 4A and 4B and 4C, 5A and 5B and 5C, 6A and 6B and 6C, and 7A and 7B and 7C, shows respectively a front view ("A" drawing) and a cross section ("B" drawing) and a side view ("C" drawing) of various narrow point intracorneal inserts made according to the invention. Although these drawings show narrow points on the inventive inserts, such points are not a critical aspect of the invention. The ends of the inserts may be tapered in both width and thickness, in one or the other of those axes, or may be blunt. Other variations of the ends will be discussed below to the extent necessary to understand the invention. These inserts are "pre-formed" or "pre-shaped". By the use of these terms, I mean that the insert has sufficient structural integrity to approximate in shape some portion of the intrastromal channel into which it is to be placed.

Figure 4A:
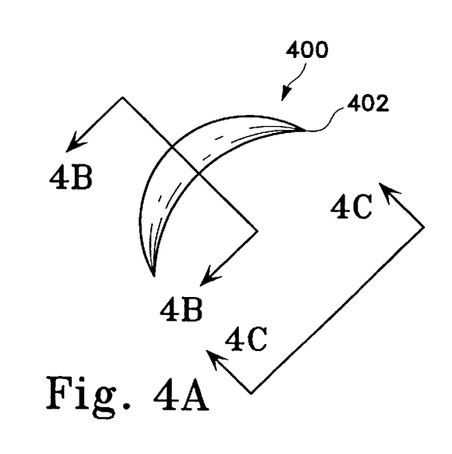
Figure 4B:
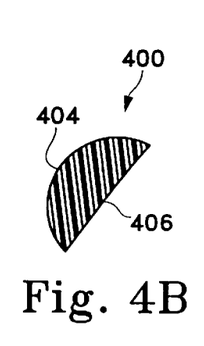
Figure 4C:
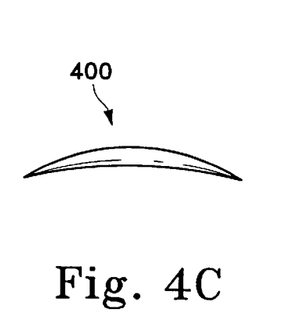

FIG. 4A shows a front view of a pre-shaped intracorneal insert (400) having ends (402). The intracorneal insert tapers both in width and in thickness to narrow points (402). Viewed in cross section in FIG. 4B, the generally smooth convex front surface (404) and planar rear surface (406) may be seen. FIG. 4C shows a side view of the segment or insert. Some care must be taken in using an insert having such narrowly pointed ends since such inserts are intended to be introduced into a previously created intrastromal channel. Points of great sharpness may wander in direction from the desired channel.

Figure 5A:
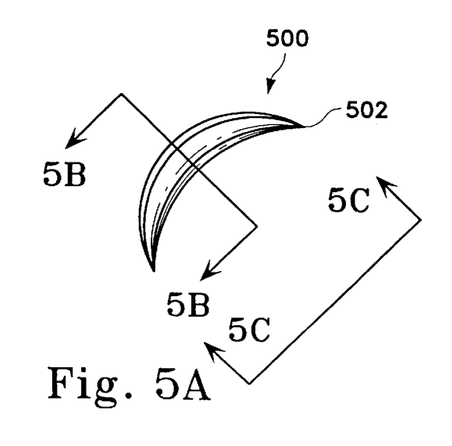
Figure 5B:
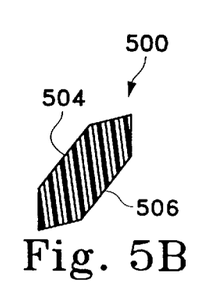
Figure 5C:
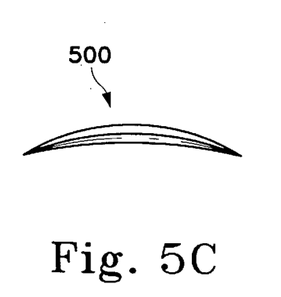

FIG. 5A shows a front view of an intracorneal insert (500) having ends (502). Again, the intracorneal insert tapers both in width and in thickness to narrow points (502). Viewed in cross section in FIG. 4B, the generally hexagonal shape may be seen. The surfaces most adjacent the anterior surface of the eye and the side just opposite are generally the two longer of the sides. Those generally planar front surface (504) and planar rear surface (506) may be seen. Our previous experience with Intracorneal Rings has demonstrated that the use of such a shape in the cornea is generally less traumatic than one of a rectangular cross section and yet, because of the similarity of the shape to that of the intrastromal formed by the blade producing the channel, is often considered to be the maximum cross sectional volume achievable in such configuration. FIG. 5C shows a side view of the segment or insert.

Figures 6A, 7A:
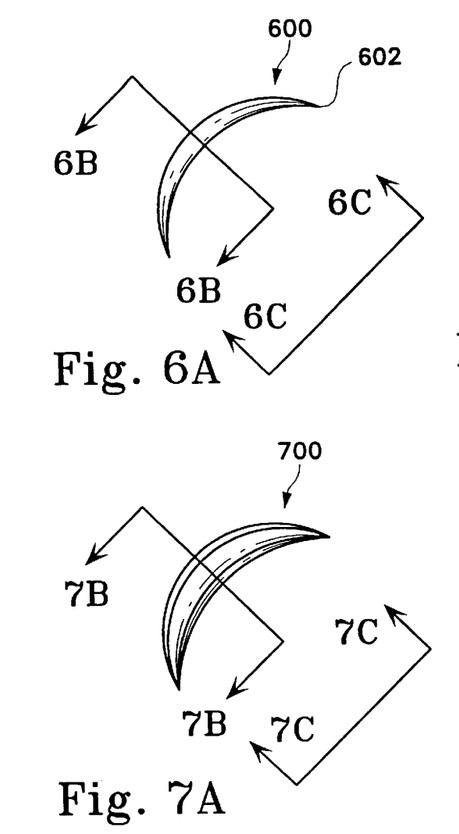
Figures 6B, 6C:
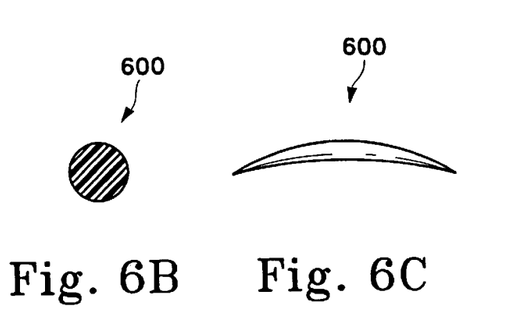

FIG. 6A shows a front view of an intracorneal insert (600) having ends (602). The intracorneal insert tapers both in width and in thickness to narrow points (502). FIG. 6B shows the generally round cross section. The cross section may also be oval-shaped with the major axis of the oval either as the width or the thickness or neither. FIG. 6C shows a side view of the segment or insert which, because of the symmetry of the device, is the same as the top view.

FIG. 7A shows a front view of a hybrid intracorneal insert (700) having ends (702). Again, the intracorneal insert tapers both in width and in thickness to narrow points (702). Viewed in cross section in FIG. 5B, the generally hexagonal shape may be seen. This set of Figures is to show the concept of a multilayered insert made up of polymers of different characteristics. In this example of a multi-layered insert, the hybrid intrastromal segment has inner (702) and outer faces (704) of polymers having low moduli of elasticity. Low modulus polymers are those having a modulus of elasticity below about 3.5 kpsi, more preferably between 1 psi and 1 kpsi, and most preferably between 1 psi and 500 psi. They must be physiologically compatible with the eye. As was noted above, this class of polymers includes most polymeric materials used in soft contact lenses.

Figure 7B:
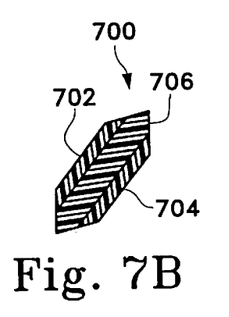

The inner portion or core (706) as shown in FIG. 7B may be a physiologically compatible polymer having a high modulus of elasticity. A high modulus of elasticity is considered to be greater in value than about 3.5 kpsi, preferably 5–12 kpsi, and most preferably 8–10 kpsi. These high modulus of elasticity polymers are discussed above.

If hydratable polymers are chosen for the outside layers, the extent to which those outer layers swell upon hydration is dependent upon the type of polymer chosen and, when the polymer is hydratable, upon the amount of cross-linking found in the outer layers (702) and (706), and upon the thickness of the layer. Generally speaking, the more highly linked the hydratable polymer, the smaller the amount of volume change upon hydration. Conversely, a polymer having only sufficient cross-linking for strength in the service in which this device is placed, will have a somewhat lower level of cross-linking. Alternatively, a substantially nonswellable polymer system may be formed of a hydrogel physically interpenetrated by another polymer which does not hydrate, e.g., polyHEMA.

The thickness of the outer layer depends in large function upon the intended use of the intrastromal segment. If the outer layer is used to provide a swellable outer layer which does not add significantly to the size of the intrastromal segment or is used functionally as a lubricant layer, the other layer may be quite thin—even to the point of a layer of minimum coverage, perhaps as thin as a single molecular layer.

Of course, the inner and outer layers need not be, respectively, low modulus and high modulus polymers but may instead be multiple layers of low modulus polymers including an outer hydrophilic polymer layer and an inner hydrophobic polymer; a variety of hydrophilic polymers; etc.

Figure 7C:
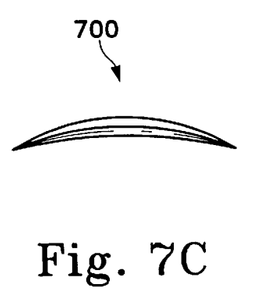

Additionally, the inventive device shown in FIGS. 7A to 7C need not have a inner (704) and outer (702) layers over the entire intrastromal segment. For instance, to alleviate astigmatism, an intrastromal segment having a thicker portion and a substantially thinner portion may be desired. An intrastromal segment having an inner core of a high modulus polymer and an outer covering of a swellable polymer might be chosen. The surgeon would remove a portion of the intrastromal segment's exterior coating or face prior to introducing the intrastromal segment into the eye. Further, and as will be discussed below in greater detail, hydrophilic polymers are more easily infused with therapeutic and diagnostic materials than are the high modulus materials. In the variation just noted, the insert may then be used to deliver the infused therapeutic and diagnostic materials in a greatly delimited of treatment or diagnostic area.

Figure 8A:
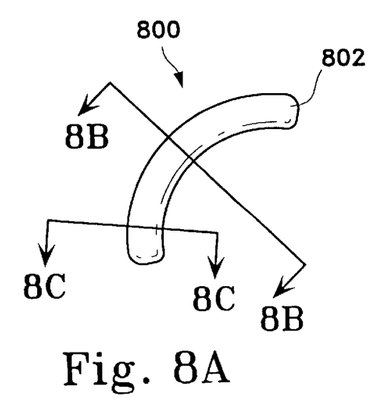
FIGS. 8A, 8B, and 8C show respectively a front view and two cross sections of a broad point tapered intracorneal insert made according to the invention.
Figure 8B:
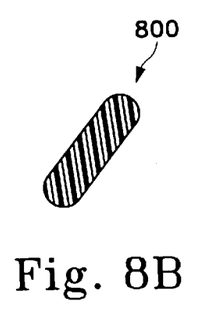
Figure 8C:
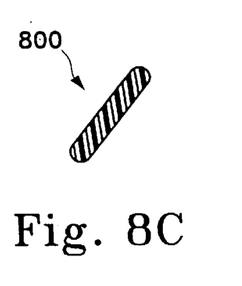

FIG. 8A shows a front view of an wide end intracorneal insert (800) having ends (802). In this variation, the insert tapers only in thickness to form a spade-shaped end (802). Viewed in cross section in FIG. 8B, the generic shape may be seen. FIG. 8C shows the same shape but nearer to the end of the device. This set of Figures is to show the concept of a single-tapered end.

Figure 9A:
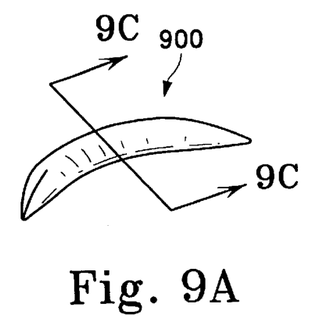
FIGS. 9A, 9B, and 9C show respectively a front view and two cross sections of a soft, filled intracorneal insert made according to the invention.
Figure 9B:
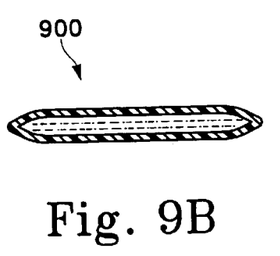
Figure 9C:
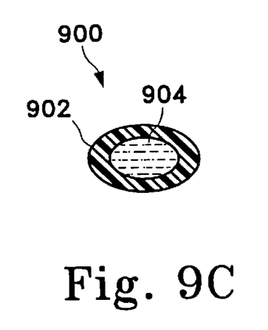

FIG. 9A is a front quarter view of a variation of the intrastromal segment (900) made of a low modulus polymer system hydratable outer coating (902). FIG. 9C shows the inner cavity (904). This intrastromal segment may be inserted into the intrastromal space created by the dissector as a covering on a tool similar to the dissector which created the intracorneal channel. Once in position the insertion tool is rotated out of the intrastromal segment leaving the shell within the stroma.

FIG. 9C shows the inner cavity (904) which may be filled with a biologic, a drug or other liquid, or biologically active eye treatment material. These devices may be tied or pinched or crimped or otherwise connected at their point of insertion by known techniques.

The shell (902) may be injected with a settable soft polymer core, allowed to expand to a desired thickness, and set. Polymeric gels which do not polymerize in situ are preferred. Suitable injectable polymers are well known but include polyHEMA hydrogel, cross-linked collagen, cross-linked hyaluronic acid, siloxane gels, and organic-siloxane gels such as crosslinked methyl vinyl siloxane gels.

Figure 10:
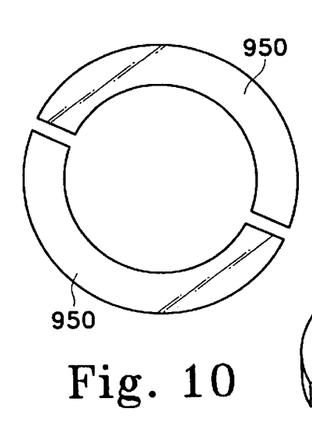
FIG. 10 depicts a front view of an end-to-end assemblage of intracorneal segments having no end junctions between the inserts.

FIG. 10 shows a variation of the invention in which an assemblage of the inventive intrastromal segments (950) are formed into a polymeric ring or, at least, into an assemblage which totals no more than 360° of corneal circumference when assembled into the intracorneal space. The two segments (950) depicted in FIG. 10 may be of any of the individual variations shown in the Figures above and need not be connected in any way. The segments may be of similar or quite different configurations depending upon the indication to be remedied. Additionally, they may be inserted in separately produced intrastromal channels which may, or may not, be in communication within the cornea. Such individual insertion will be discussed in more detail below.

Figure 11:
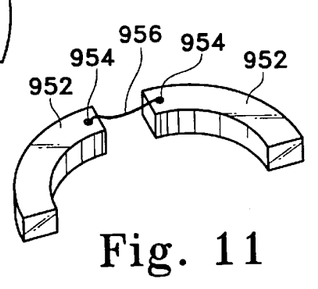
FIG. 11 shows a front view of an end-to-end assemblage of intracorneal segments having junctions between the inserts to hold them in a particular spatial relationship.

FIG. 11 shows a similar assemblage in which the intracorneal segments (952) are held together using open holes (954) and a clip (956) which may be a simple wire or other suitable joining device. An assemblage such as is seen in FIG. 11 may be advantageously inserted from a single central opening, as will be described below.

Figure 12:
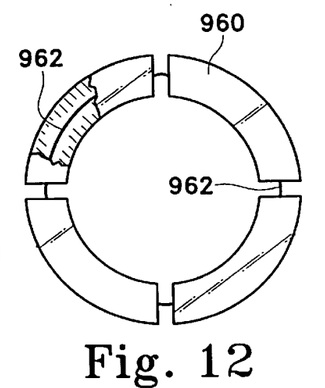
FIG. 12 shows a partial cross-sectional view of an end-to-end assemblage of intracorneal segments which are strung on a filament to form a ring.

FIG. 12 shows a variation, an assemblage of segments, in which the sections (960) are strung together on a filament (962) which has a transverse cross-section less than that of the segments (960). The segments (960) have an open pathway or channel along their length (see cutaway) which permits such stringing.

Figure 13A:
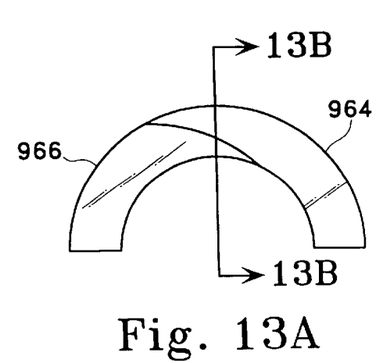
FIGS. 13A and 13B show respectively a front view and a cross section of an assemblage of intracorneal inserts made according to the invention which overlap at their ends to form a single monolithic device.
Figure 13B:
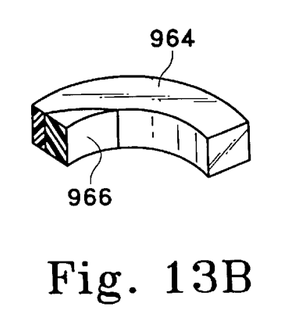

FIGS. 13A and 13B show a variation of the inventive intracorneal inserts in which two or more sections overlap to form an assemblage. Alternatively, FIGS. 13A and 13B can be described as illustrating an embodiment comprising an insert or segment including multiple sections nested one upon another. The top view shown in FIG. 13A depicts the assemblage as found in the eye. The assemblage need not be formed of segments of the same or similar width or thickness or material of construction nor need the assemblage be limited to the semicircle shown in FIG. 13A. Although a front-to-back assemblage of is depicted in FIG. 13B, the junction between the sections or segments (964 & 966) may be of any other design which allows contact between the adjoining sections and remains relatively immobile after the placement in the cornea. For instance, the design shown in FIGS. 13A and 13B involves the use of a smooth interface. The intrastromal channel normally exerts substantial force against the assemblage and will maintain the segments in the depicted relational position within the eye.

FIGS. 14A–14E schematically portray a method for the insertion of the segments described above in which partial arc segments are introduced into separate sections of the corneal circumference outside of the "sight" area of that cornea.

Figure 14A:
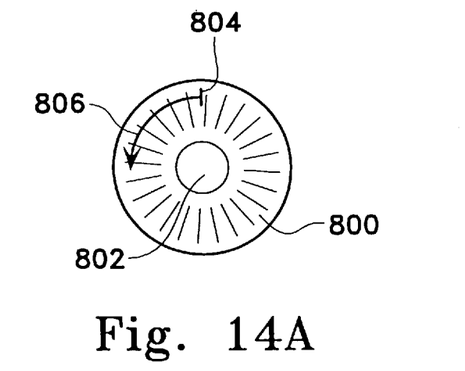
FIGS. 14A–14E and 15A–15F schematically depict procedures for installing intracorneal inserts.
Figure 14B:
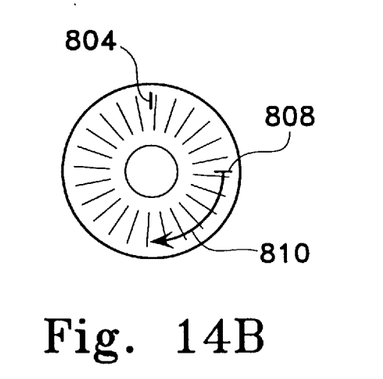

In FIG. 14A, the frontal view shows the iris (800) and the pupil (802). As was described above, the cornea is clear and is not visible in these drawings. Insertion of the inventive device is a reasonably simple surgical procedure. An entry slit (804) is made radially into the cornea. A dissector blade is introduced into the entry slit (804) and turned in the direction of the arrow (806) to form a partial intrastromal channel of a desired length. A second entry slit (808) may then be made in the cornea and a second intrastromal channel be made in the direction of the arrow (810).

Figure 14C:
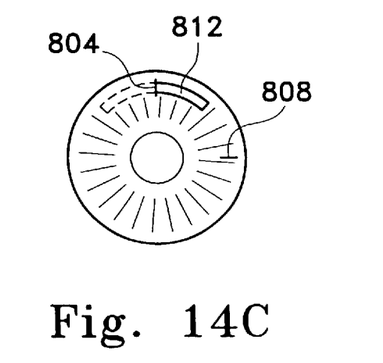
Figure 14D:
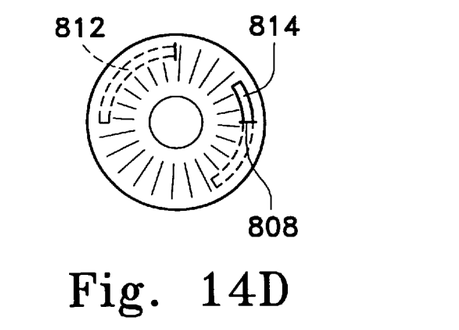
Figure 14E:
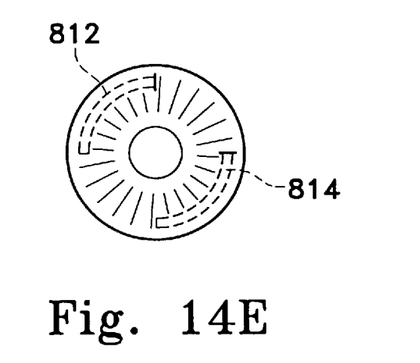

FIG. 14C shows the introduction of the first inventive segment (812) into the first entry slit (804). FIG. 14D shows the first segment (812) in its final resting position and the introduction of the second segment (814) into the second entry slit (808). Finally FIG. 14E shows both first segment (804) and second segment (814) in their final position within the cornea. This demonstrates the flexibility of the procedure in that either left or right "hand" insertion is appropriate and the intrastromal channel need ont be a complete circle about the cornea.

FIGS. 15A–15F schematically portray a method for the insertion of the segments described above in which partial arc segments are introduced into separate sections of the corneal circumference outside of the "sight" area of that cornea through a single entry slit.

Figure 15A:
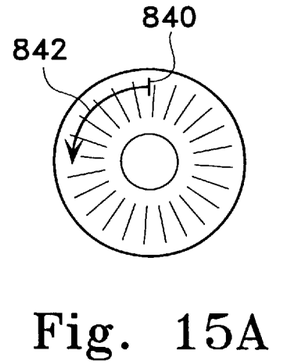
Figure 15B:
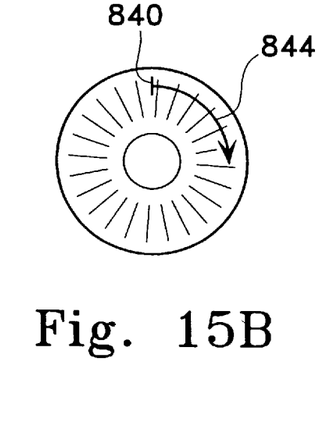

FIG. 15A shows the making of the initial entry slit (840) radially into the cornea. A dissector blade is introduced into the entry slit (840) and turned in the direction of the arrow (842) to form a partial intrastromal channel of a desired length. As is shown in FIG. 15B, a second intrastromal channel is made in the direction of the arrow (844) from the same entry slit (842).

Figure 15C:
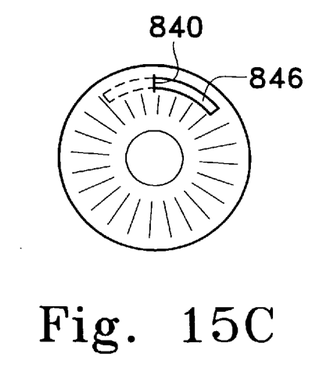
Figure 15D:
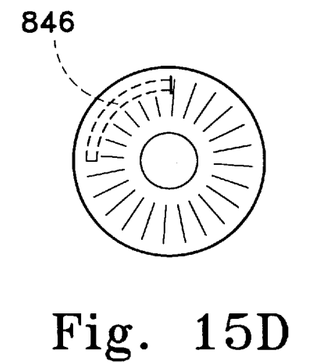
Figure 15E:
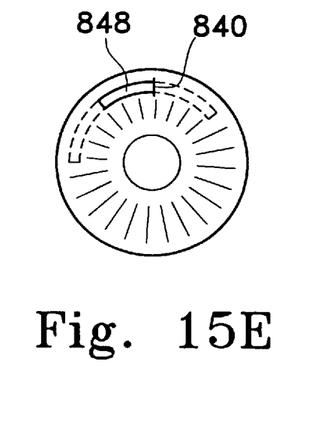
Figure 15F:
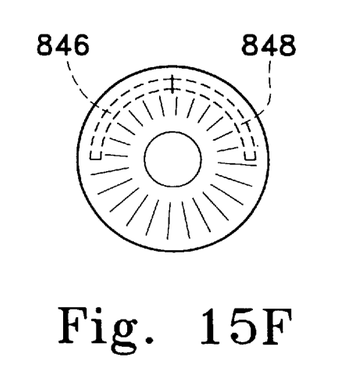

FIG. 15C shows the introduction of the first segment (846) into the entry slit (842). FIG. 15D shows the first segment (846) in its final resting position. FIG. 15D shows the introduction of the second segment (848) into the entry slit (840). Finally FIG. 15F shows both first segment (846) and second segment (848) in their final position within the cornea.

Because of the nature of certain of these inserts, a large measure of adaptability is available in the process of inserting the devices. For instance, I have found that when using various inserts (particularly with ocular lubricants) that the inserts may be "pushed" nearly 180° around a previously created intrastromal channel for insertion and then easily removed, if so desired. This observation means that the following procedure may be used. The eye of a person having myopia and/or astigmatism may be measured to determine the proper amount of correction needed. From this information, the size and placement of one or more segments may then be chosen. For instance, the selected sections might be two inserts of 30° arc angle and 100 mils×100 mils cross section at two opposing meridian. After insertion in the appropriate channels, the vision of the eye might again be measured. If insufficient correction of an indication is found, the insert may be withdrawn and a larger size selected and inserted. If an astigmatic aberration is introduced, the insert may be withdrawn (partially or completely) and trimmed prior to complete re-insertion. Such adjustability is not normally available when dealing with gel-based rings or with surgical techniques based on radial keratotomy.

The terms and expressions which have been used in the description above are used only as terms of description and not of limitation. There is no intention of excluding equivalents of the features shown or described. It is recognized that one having ordinary skill in this art would perceive equivalence to the inventions claimed below, which equivalence would be within the spirit of the invention as expressed above.

I claim as my invention:

1. An intracorneal insert for introduction into the cornea of a human eye, said insert comprising an arcuate, physiologically compatible synthetic, polymeric segment having a predetermined shape prior to implantation in the cornea, said segment subtending an arc substantially less than 360° and being adapted for implantation within a human cornea and configured for altering the shape of the cornea by substantially a predetermined amount, said segment being constructed to substantially retain said predetermined shape over time after implantation in the cornea.

2. The insert of claim 1 wherein the segment subtends an arc less than about 320°.

3. The insert of claim 2 wherein the segment subtends an arc less than about 270°.

4. The insert of claim 3 wherein the segment subtends an arc of 20° to 90°.

5. The insert of claim 2 wherein the segment comprises a physiologically compatible polymer having a low modulus of elasticity.

6. The insert of claim 5 wherein the low modulus physiologically compatible polymer is selected from the group consisting of polyhydroxyethylmethylacrylate (Poly-HEMA), polyvinylpyrrolidone (PVP), polyethylene oxide, polyacrylates, polyacrylic acid and its derivatives, their copolymers and interpolymers, silicones, crosslinked dextran, crosslinked heparin, and hyaluronic acid.

7. The insert of claim 6 wherein the low modulus physiologically compatible polymer is selected from polyhydroxyethylmethylacrylate (Poly-HEMA) and polyvinylpyrrolidone (PVP).

8. The insert of claim 5 further comprising a drug or biologic agent.

9. The insert of claim 8 wherein the drug or biologic agent is selected from the group consisting of dexamethasone, heparin, corticosteroids, antimitotics, antifibrotics, antiinflammatory, anti-scar-forming, anti-adhesion, antithrombogenic, and antiangiogenesis factors.

10. The insert of claim 9 where the drug or biologic agent comprises an antiinflammatory or antithrombogenic.

11. The insert of claim 2 wherein the segment comprises a polymer having a high modulus of elasticity.

12. The insert of claim 11 wherein the polymer having a high modulus of elasticity is one or more members selected from the group consisting of PMMA, polytetrafluoroethylene, polysulfones, polycarbonate, epoxies, a polyolefin selected from polyethylene, polypropylene, polybutylene, mixtures, and interpolymers.

13. The insert of claim 12 where the polymer having a high modulus of elasticity comprises PMMA.

14. The insert of claim 1 wherein the segment has a cavity formed therein.

15. The insert of claim 14 further comprising a drug or biologic agent disposed in said cavity.

16. The insert of claim 15 wherein the drug or biologic agent is selected from dexamethasone, heparin, corticosteroids, antimitotics, antifibrotics, antiinflammatories, anti-scar-forming, anti-adhesion, antithrombogenic, and antiangiogenesis factors.

17. The insert of claim 16 wherein the drug or biologic agent comprises an antiinflammatory or antithrombogenic.

18. The insert of claim 1 further comprising an ocular lubricant.

19. The insert of claim 18 wherein the ocular lubricant is selected from the group consisting of hyaluronic acid, methylethylcellulose, dextran solutions glycerine solutions, polysaccharides, and oligosaccharides.

20. The insert of claim 1 further including a coupling member coupled to said segment coupling the insert to another one of said segments.

21. The insert of claim 1 in combination with another one of said segments, said segments being coupled to one another to form an assemblage.

22. The insert of claim 21 wherein the shape of one segment differs from that of the other.

23. The insert of claim 21 wherein said segments have similar thicknesses.

24. The insert of claim 1 wherein said segment comprises at least two polymeric layers.

25. The insert of claim 24 where at least one of said polymeric layers comprises a low modulus physiologically compatible polymer.

26. The insert of claim 25 where at least one of said polymeric layers comprises a high modulus physiologically compatible polymer.

27. The insert of claim 1 wherein said segment includes a channel formed therein.

28. The insert of claim 27 further including a member extending through said channel and extending from said segment.

29. The insert of claim 1 wherein said segment comprises multiple sections.

30. The insert of claim 29 wherein said sections are nested.

31. The insert of claim 1 wherein said segment is configured and adapted for implantation within a human cornea for altering the shape of the cornea by substantially a predetermined amount when positioned completely below the anterior surface of the cornea.

32. An intracorneal insert for introduction into the cornea of a human eye, said insert comprising an arcuate, physiologically compatible synthetic, polymeric segment having a predetermined shape prior to implantation in the cornea, said segment subtending an arc substantially less than 360° and being adapted for implantation within a human cornea and configured to alter the topography of the cornea in a manner that effects correction of a predetermined refractive disorder of the eye, said segment being constructed to substantially retain said shape over time after implantation within the cornea.

33. The insert of claim 32 wherein the segment subtends an arc less than about 320°.

34. The insert of claim 33 wherein the segment subtends an arc less than about 270°.

35. The insert of claim 34 wherein the segment subtends an arc of 20° to 90°.

36. The insert of claim 33 wherein the segment comprises a physiologically compatible polymer having a low modulus of elasticity.

37. The insert of claim 36 wherein the low modulus physiologically compatible polymer is selected from the group consisting of polyhydroxyethylmethylacrylate (Poly-HEMA), polyvinylpyrrolidone (PVP), polyethylene oxide, polyacrylates, polyacrylic acid and its derivatives, their copolymers and interpolymers, silicones, crosslinked dextram, crosslinked heparin, and hyaluronic acid.

38. The insert of claim 37 wherein the low modulus physiologically compatible polymer is selected from polyhydroxyethylmethylacrylate (Poly-HEMA) and polyvinylpyrrolidone (PVP).

39. The insert of claim 36 further comprising a drug or biologic agent.

40. The insert of claim 39 wherein the drug or biologic agent is selected from the group consisting of dexamethasone, heparin, corticosteroids, antimitotics, antifibrotics, antiinflammatory, anti-scar-forming, anti-adhesion, antithrombogenic, and antiangiogenesis factors.

41. The insert of claim 40 wherein the drug or biologic agent comprises an antiinflammatory or antithrombogenic.

42. The insert of claim 33 wherein the segment comprises a polymer having a high modulus of elasticity.

43. The insert of claim 42 wherein the polymer having a high modulus of elasticity is one or more members selected from the group consisting of PMMA, polytetrafluroethylene, polysulfones, polycarbonate, epoxies, a polyolefin selected from polyethylene, polypropylene, polybutylene, mixtures, and interpolymers.

44. The insert of claim 43 wherein the polymer having a high modulus of elasticity comprises PMMA.

45. The insert of claim 32 additionally comprising an ocular lubricant.

46. The insert of claim 45 wherein the ocular lubricant comprises a material selected from the group consisting of hyaluronic acid, methylethylcellulose, dextran solutions, glycerine solutions, polysaccharides, and oligosaccharides.

47. The insert of claim 32 further including a coupling member coupled to said segment for coupling the insert to another one of said segments.

48. The insert of claim 32 in combination with another one of said segments, said segments being coupled to one another to form an assemblage.

49. The insert of claim 32 wherein said segment is configured and adapted for implantation within a human cornea for altering the topography of the cornea in a manner that effects correction of a predetermined refractive disorder of the eye when positioned completely below the anterior surface of the cornea.

50. An assemblage for introduction into the cornea of a human eye, said assemblage comprising multiple physiologically compatible, arcuate segments, each having a predetermined shape, each subtending an arc less than 360° and being adapted for implantation within a human cornea and configured for altering the shape of the cornea by substantially a predetermined amount, each segment being constructed to substantially retain said predetermined shape over time after implantation in the cornea and each segment being coupled to another one of said segments.

51. The assemblage of claim 50 wherein said segments are arranged to form portions of a ring and have a combined arc length less than 360°.

52. The assemblage of claim 51 wherein said segments are arranged in a plane.

53. The assemblage of claim 51 wherein said segments are spaced from one another.

54. The assemblage of claim 50 wherein at least one segment includes overlapping sections.

\* \* \* \* \*